US00PP17211P2

(12) United States Plant Patent
Gargiulo

(10) Patent No.: US PP17,211 P2
(45) Date of Patent: Nov. 14, 2006

(54) GRAPEVINE '90-3618'

(50) Latin Name: *Vitis vinifera*
Varietal Denomination: 90-3618

(75) Inventor: Angel A. Gargiulo, San Rafael (AR)

(73) Assignee: L&M Nursery, Delano, CA (US)

( * ) Notice: Subject to any disclaimer, the term of this patent is extended or adjusted under 35 U.S.C. 154(b) by 526 days.

(21) Appl. No.: 10/382,081

(22) Filed: Mar. 4, 2003

(51) Int. Cl.
*A01H 5/00* (2006.01)

(52) U.S. Cl. ..... Plt./205

(58) Field of Classification Search ..... Plt./205
See application file for complete search history.

*Primary Examiner*—Kent Bell
*Assistant Examiner*—June Hwu
(74) *Attorney, Agent, or Firm*—Jondle & Associates P.C.

(57) ABSTRACT

The new grape cultivar '90-3618' can best be characterized as a large, productive, seedless, dark table grape with excellent quality for handling abilities. The berries of the new cultivar are sweet and firm with very strong attachment and almost no shatter at commercial maturity. The berries reach full maturity in early to mid-September.

1 Drawing Sheet

Genus and species: *Vitis vinifera.*

BACKGROUND AND SUMMARY OF THE INVENTION

The new dark red table grapevine '90-3618' is of *Vitis vinifera* parentage and resulted from a two year breeding program which had as its goal the development of a red, seedless, sweet-flavored table grape. The hybridization resulting in '90-3618' was made near Delano, Calif. in 2001. The new selection was then propagated by cuttings and grafting to 'Salt Creek' (unpatented) rootstock. Vines were subsequently treated with gibberellic acid. The present invention has been found to retain its distinctive characteristics through successive asexual propagations.

ORIGIN OF THE NEW VARIETY

The parents of grapevine '90-3618', are 'Red Globe' (unpatented) and '26916' (unpatented). The new variety was developed during the 2001 and 2002 growing seasons near the Delano, Calif. region, by cross pollination between the grapevine 'Red Globe' and grapevine '26916'. The subject variety is similar to grapevine '90-3437' (U.S. Ser. No. 09/935,491) but has distinct differences in berry color, ripening time and bunch density. Grapevine '90-3618' has been asexually reproduced by taking dormant cuttings (2 buds long) from the mother vine, located at a vineyard near Delano, Calif., and grafting the cuttings onto rootstock in existing vineyards. Grapevine '90-3618' has also been asexually reproduced in a vineyard near Delano, Calif. by taking dormant cuttings (6 buds long) and planting the cuttings into the ground on its own roots.

DESCRIPTION OF THE FIGURES

The accompanying drawing illustrates the following:

Fruit cluster at harvest, including bunches of grapes, sectioned portions of individual berries, typical foliage and segments of canes.

DETAILED BOTANICAL DESCRIPTION OF THE INVENTION

The following description of grapevine '90-3618' contains references to color names taken from the "Dictionary of Color", by Maerz and Paul, 1st edition published in 1930.

Descriptions of the new invention apply to vines of '90-3618' spaced approximately 2.4 meters down the row and 3.66 meters between the rows. The vine canopy extends from 0.75 to 1.0 meters out into the row. The new variety has been propagated onto grape rootstock that was 7 years old in 2001. The varietal top itself is three years old. The new variety '90-3618' was grown near Delano, Calif. during the growing seasons of 2001 and 2002. Descriptions of the new invention apply to vines of grapevine '90-3618' grown on 'Salt Creek' rootstock. These descriptions are believed to apply generally to the new variety grown under similar circumstances elsewhere.

VINE

General:

*Size.*—The test grapevines of '90-3618' are planted approximately 2.4 meters down the row and 3.66 meters between the rows. The vine canopy extends from 0.75 to 1.0 meters out into the row. The new variety has been propagated onto 'Salt Creek' grape rootstock that was 7 years old in 2001. The varietal top itself is three years old.

*Vigor.*—Very vigorous, and slightly more vigorously than 'Thompson Seedless'.

*Productivity.*—Productive, equal to the productivity of 'Thompson Seedless'. The subject variety has been trained to a bilateral cordon and is spur pruned.

Trunk:

*Surface texture.*—Rough textured and somewhat shaggy and furrowed.

*Bark color.*—Varies from dark grey (6-A-8) to a lighter grey (4-A-8).

*Trunk circumference.*—5.8 cm to 7.8 cm at 40 cm height from the ground.

MATURE CANES

Size:

*Thickness.*—Varies from average to slightly above average.

Larger canes that arise from the dormant spurs attain a diameter ranging from 10 to 20 mm, depending on the degree of light exposure and the height in the canopy. The diameter is measured at the base of the cane. The cane cross sectional form is most frequently globose.

Surface: Finely and uniformly striated.

Color: Ranges from light tan-brown (12-C-4 Malacca brown) to a darker brown (12-B-7).

Internode length: 12 to 19 cm on the stronger upper suncanes and from 10 to 15 cm on the canes found lower in the canopy.

TENDRILS

Length: Relatively long ranging from 25 to 30 cm.

Diameter: Varies from 2.0 to 2.5 cm in thickness, measured at the base of the tendril.

Distribution: Discontinuous.

Form: Predominantly bifid, although trifid tendrils may be present.

Color: When young is a light, shiny green (17-K-3).

GROWING TIPS

The tip indumenta is very sparsely pubescent and is most distinctly seen along the mid-vein on the under side of the leaf.

Color: Of the expanding shoot tip varies from a yellow-green (17-L-3 Endive yellow) to a green-bronze (12-L-1 Oil Yellow).

LEAVES

Mature leaves:

*Average blade length.*—12 cm to 16.4 cm as measured from the apex of the center leaf lobe to the petiolar junction.

*Size of blade.*—Large usually having 5 lobes.

*Shape.*—Pentagonal.

*Shape of teeth along leaf margins.*—Convex sides.

*Length of teeth along leaf margins.*—Medium to Large and variable, 3–9 mm in length.

*General shape of petiole sinus.*—Open with no basal lobe overlap, U-shaped with no marginal teeth.

*Shape of upper leaf sinus.*—Vary from slightly open to slightly closed.

Leaf color:

*Upper leaf surface.*—Shiny and ranges from a medium green (22-L-2 Palm green) to a darker green (23-J-4 Lincoln green).

*Lower leaf surface.*—Rather dull and lighter in color, ranging from grey-green (21-K-2 ) to a darker green (21-J-6).

*Upper leaf veins.*—Yellowish-green, especially basally (20-K-2 ) to (20-K-5). No red anthocyanin coloration visible.

*Lower leaf veins.*—Prominent ranging from light yellow-green (18-I-3) to a darker (19-J-5). No red anthocyanin coloration present in most cases. Occasionally, a slight amount of pale purple-rose (4-F-2) color is present near the base of the mid-vein.

*Surface texture.*—Smooth glabrous, with only slight rugosity.

*Surface appearance.*—Dull.

Lower surface:

*Surface texture.*—Glabrous, with only a slight amount of pubescence near the base of the mid-vein.

Leaf petiole:

*Length of petiole.*—13.4 to 17.2 cm.

*Petiole thickness.*—3.0 to 4.0 mm measured at mid petiole.

*Petiole shape.*—Glabrous.

*Petiole color.*—Pale green (17-J-6) to a lighter green-yellow (17-J-2).

*Mature petiole leaf color.*—At leaf blade base, frequently tinged with a purplish-rose hue. This anthocyanin coloration varies from a rose color (2-D-3) to a darker purple-rose (4-E-4).

*Length of petiole compared to middle vein.*—Considerably shorter.

*Sinus.*—Open, with no basal love overlap, U-shaped, no marginal teeth.

FLORAL CLUSTER DESCRIPTION

Bloom timing: Date of full bloom was May 11, 2002. Date of the first bloom occurred approximately 8 days previous to full bloom on approximately May 3, 2002.

Cluster form: Long and tapered.

First floral cluster: Can occur from third to fifth node produced from the dormant spur. Most frequently, the first floral cluster occurs on the fourth node.

Floral cluster frequency: Medium, imparting the potential for normal cropping.

Floral cluster length: At 80% bloom, length varies from 14.5 to 28 cm, not including the peduncle.

Floral cluster width: 3.5 to 9.5 cm.

Cluster peduncles: length 4.0 to 8.0 cm, thickness 3.0 to 6.0 mm.

Inflorescence: Hermaphroditic.

*Floral stamens.*—Upright with normal size anthers.

*Pollen amount.*—Abundant.

*Pollen color.*—Pale yellow.

*Calyptra separation from the flower base.*—Complete.

*Duration of bloom.*—Average 10 to 12 days, depending on ambient temperatures during the bloom period.

Cluster petiole coloration: Medium green (22-K-3).

Calyptra color: Bright green (21-L-6 Parrot green).

Floral anthers: Light yellow (17-G-1).

Developing tendrils color: At bloom is shiny, bright green (19-L-4).

FRUIT DESCRIPTION—PRIMARY CLUSTER

Date of maturity: First pick Sep. 10, 2001, with completion of harvest by Sep. 20, 2001.

Bunch size: Medium to large.

*Bunch length.*—26 to 32 cm, not including the peduncle.

*Bunch width.*—18 to 24 cm.

*Bunch form.*—Tapered, moderately broad at the shoulders and narrowing near the base.

*Bunch weight (natural).*—469 g.

*Bunch weight (treated with gibberellic acid).*—1362 g.

Bunch density: Relatively loose with numerous pedicels visible in lateral aspect.

*Berry count.*—Vary from 103 to 256 in the largest clusters.

*Peduncle length.*—Varies from 3.2 to 5.5 cm.

*Peduncle thickness.*—Ranges from 3.1 to 5.5 mm at the peduncle base.

*Peduncle color.*—Medium green (12-K-1), with areas of light brown-green (14-K-5) to brown (14-H-8) often present.

Berry form: Lateral aspect can range from globose to broadly oval, occasionally a few obovate form berries can be found within the cluster.

Cross sectional view berry form: Globose.

Berry size: Large from 21 to 27 mm in width and 25 to 29 mm in length.

Berry weight (natural): 6.5 g.

Berry weight (treated with gibberellic acid): 12 g.

Berry uniformity: Good within the individual clusters.

Berry pedicel: Average size.

*Length.*—6 to 10 mm.

*Thickness.*—1.5 to 2.0 mm.

*Color.*—Light green (19-J-5) to a greenish-brown (13-J-2).

*Attachment.*—Very strong with almost no shatter at commercial maturity.

Berry skin color: Uniform.

*Exterior.*—Most berries are 100% colored.

*Interior.*—Range from 85–100% colored.

Berry skin thickness: Medium for species.

Berry skin surface texture: Smooth and glabrous.

Berry skin, tenacity to flesh: Skin is tenacious to the flesh.

Berry skin, tendency to crack: Does not have a tendency to crack.

Berry skin, reticulation: Surface is smooth with no reticulations present.

Berry color: Ranges from bright red-purple (6-L-7) to a darker (7-L-8).

Ground color: Ranges from 0–15% of the berry surface.

*Location.*—At the basal end of the berry, next to the stem.

*Color range.*—Pale greenish color (14-A-7) with overtones of Rose to a more greenish (13-L-2).

Berry surfaces: Uniformly covered with a waxy, grayish bloom.

Berry flesh color: Somewhat variable, entire flesh area generally translucent.

*Interior color.*—Ranges from light rose-pink (1-G-1) to a very light translucent green (12-K-1). The greenish areas are almost always found in the central region of the berry.

Juiciness of flesh: Similar to standard commercial table grape varieties.

Berry firmness: Similar to standard commercial table grape varieties.

Berry juice: At commercial maturity is clear.

Solids-sugar percentage (at maturity): 20.6%.

pH of berry juice: 3.74.

Titratable acidity: 0.44 mg/ 100 mL of juice.

Seed: Full, viable seeds usually not present within the berry, although seed traces can occasionally be found.

Flavor: Very good, sweet, mild and well-balanced.

Aroma: Slight and pleasant.

Texture: Very good, berries are crisp, firm and juicy.

Use: High quality seedless type grape, well suited for commercial table grape production.

Shipping and keeping qualities of fruit: The new variety appears to store and ship similar to standard commercial table grape varieties.

Plant and fruit disease resistance/susceptibility: The new variety appears to be neither more nor less susceptible to disease and pests than standard commercial table grape varieties.

SECONDARY BUNCHES

Very few secondary bunches are present on this variety. Berry shape in the secondary bunches is similar to shape in the primary clusters but the berry size is substantially smaller. In the secondary bunches berry length ranges from 18 to 23 mm and berry diameter from 17 to 21 mm. Berries in the secondaries are usually fully colored and darker purple-red color, from (7-L-8) to a darker purple (8-H-1). Secondary bunch is irregular. Bunches range from 4 to 8.5 cm in width and from 5.0 to 9.5 cm in length. Berry counts in the secondary bunches range from as few as 5 berries up to 26 count.

COMPARISON BETWEEN PARENTAL AND COMMERCIAL CULTIVARS

Grapevine '90-3618' differs from the female parent, 'Red Globe' (unpatented) in that grapevine '90-3618' is seedless while 'Red Globe' is seeded. Grapevine '90-3618' differs from the male parent, '26916' (unpatented) in that grapevine '90-3618' is a red grape, while '26916' is a white grape.

When a comparison is made between the subject variety and the widely planted 'Thompson Seedless' grape variety, several notable differences exist. The 'Thompson Seedless' grape is a medium sized, green/yellow colored seedless grape, normally ripening in a time period between the first week of August to the first week of September in the Delano, Calif. area. The new subject variety is a large sized, dark seedless grape, normally ripening in a time period between September $10^{th}$ –$20^{th}$ in the same area. Berry shape of the 'Thompson Seedless' variety is elongated oval, while the berry shape of the subject variety is generally globose. In addition to the substantially larger berry size, the new variety has an improved berry attachment over the 'Thompson Seedless'. In contrast to the 'Thompson Seedless', the new variety has very little berry shatter at commercial maturity. The flavor of the new variety is sweet with a distinct fruity, pleasant taste. This flavor is a substantial improvement over the sweet but rather bland flavor of the 'Thompson Seedless' grape. In addition, the crisp and juicy texture of the new variety is superior to the less crisp texture of the 'Thompson Seedless' variety.

What is claimed is:

1. The new and distinct variety of grapevine '90-3618' herein described and illustrated and identified by the characteristics enumerated above.

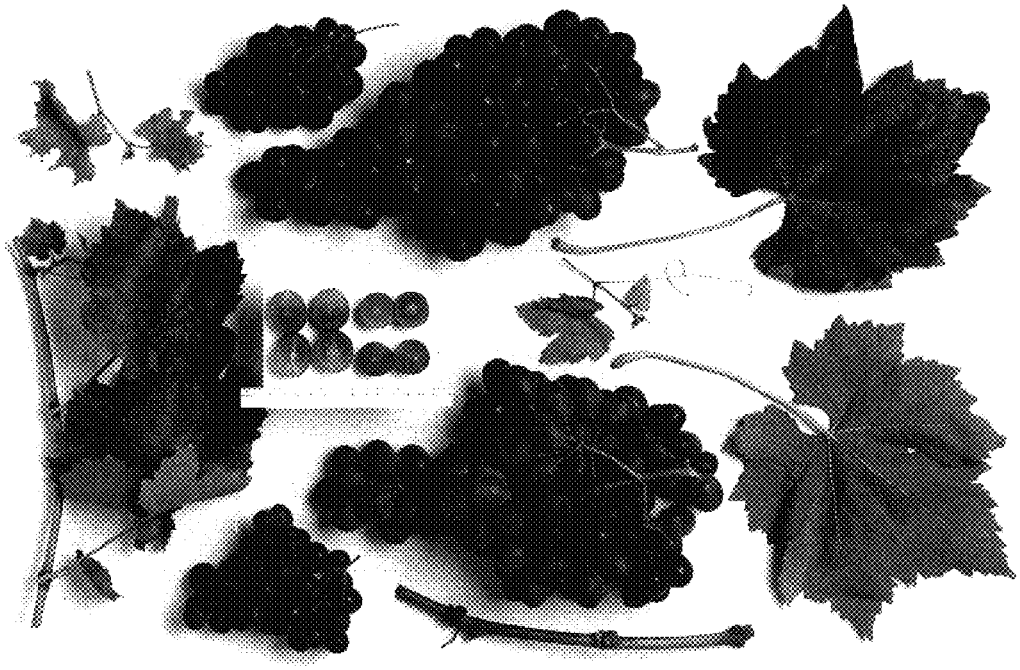

* * * * *